United States Patent [19]

Fortney

[11] 4,304,224

[45] Dec. 8, 1981

[54] POSITIVE ENVIRONMENTAL ENCLOSURE

[76] Inventor: Roger Fortney, 6421 Keelson Dr., Madison, Wis. 53705

[21] Appl. No.: 135,132

[22] Filed: Mar. 28, 1980

[51] Int. Cl.3 ........................ A61M 16/02; A61L 2/18; E04H 1/12; B01D 46/42

[52] U.S. Cl. ................................ 128/1 R; 128/201.29; 128/202.19; 55/215; 55/233; 55/279; 55/287; 55/314; 55/344; 55/350; 55/385 A; 98/33 A; 312/1; 312/3; 2/DIG. 7; 422/104; 422/120

[58] Field of Search ................. 55/215, 233, 269, 279, 55/287, 314, 344, 350, 385 A, DIG. 18, DIG. 29; 98/33 R, 33 A; 128/1 R, 1 B, 201.29, 202.19, 139; 422/104, 120; 312/1, 3; 2/DIG. 1, DIG. 7

[56] References Cited

U.S. PATENT DOCUMENTS

| | | | |
|---|---|---|---|
| 1,610,288 | 12/1926 | Jones et al. | 55/350 |
| 2,516,419 | 7/1950 | Reyniers | 128/1 R |
| 3,051,163 | 8/1962 | Trexler | 128/1 B |
| 3,239,305 | 3/1966 | Potapenko | 55/279 |
| 3,263,400 | 8/1966 | Hoke et al. | 98/33 R |
| 3,412,730 | 11/1968 | MacLeod | 128/1 R |
| 3,439,966 | 4/1969 | Perkins et al. | 312/1 |
| 3,501,213 | 3/1970 | Trexler | 128/1 R |
| 3,525,197 | 8/1970 | Sheehan | 55/233 |
| 3,601,031 | 8/1971 | Abel et al. | 55/279 |
| 3,709,210 | 1/1973 | Matthews | 312/3 |
| 4,202,676 | 5/1980 | Pelosf, Jr. et al. | 55/279 |

FOREIGN PATENT DOCUMENTS

| | | | |
|---|---|---|---|
| 2725492 | 12/1977 | Fed. Rep. of Germany | 312/1 |
| 554358 | 6/1943 | United Kingdom | 55/314 |

*Primary Examiner*—David L. Lacey

*Attorney, Agent, or Firm*—Andrus, Sceales, Starke & Sawall

[57] ABSTRACT

An environmental enclosure or clean room composed of a structural frame which supports a flexible transparent plastic film which defines a sealed chamber or room. Air is introduced into the chamber through a two-stage filter system and is exhausted through a filter duct. Located adjacent the chamber is a small entry compartment, and the entry compartment has sealed doorways leading to the exterior and to the interior of the sealed chamber respectively. To inspect objects in the sealed chamber, the operator enters the entry compartment and puts on a hermetically sealed suit that is normally stored in the compartment. With the operator sealed within the suit, the entry compartment is sterilized and the operator can then enter the main chamber. The suit has a provision for receiving air from the outside and for discharging air from the suit to the exterior of the chamber. The operator can move freely within the chamber without destroying the germ-free atmosphere in the chamber, and without the operator being contaminated by toxic or hazardous materials contained within the chamber.

12 Claims, 12 Drawing Figures

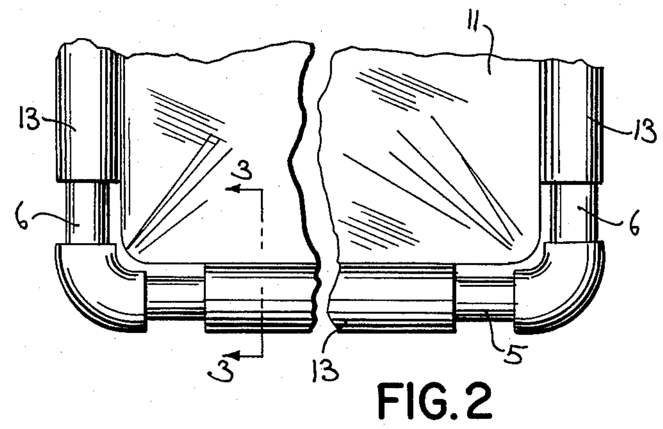
FIG. 2
FIG. 3
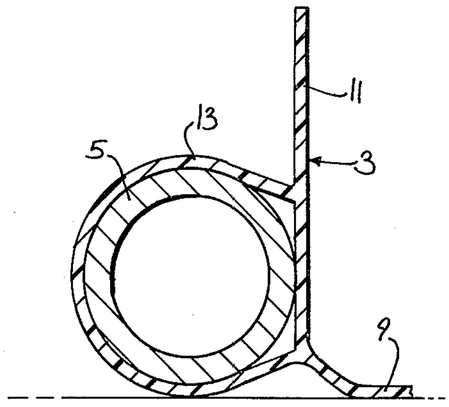
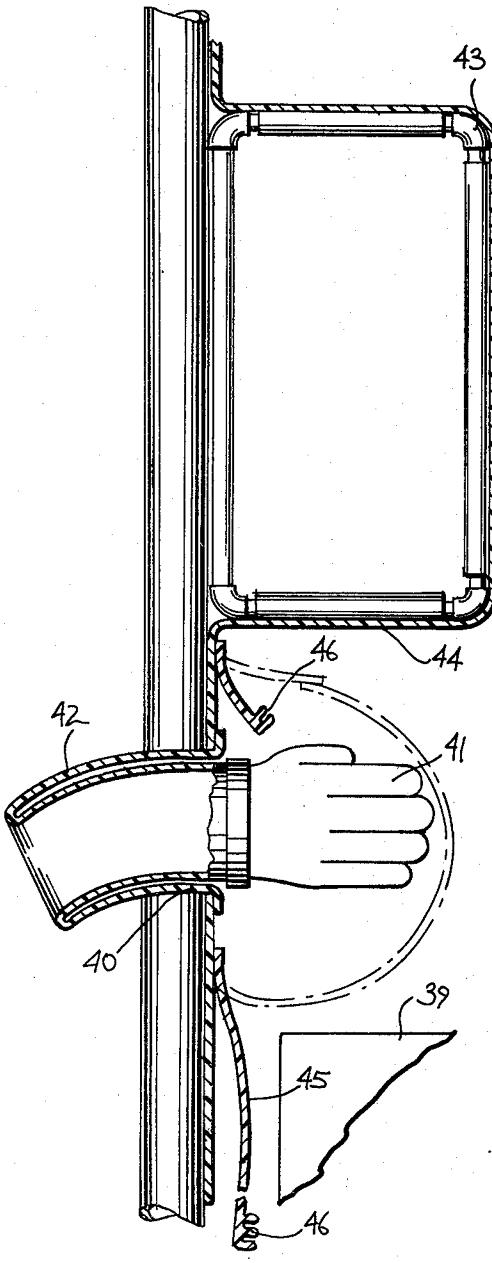
FIG. 4
FIG. 7
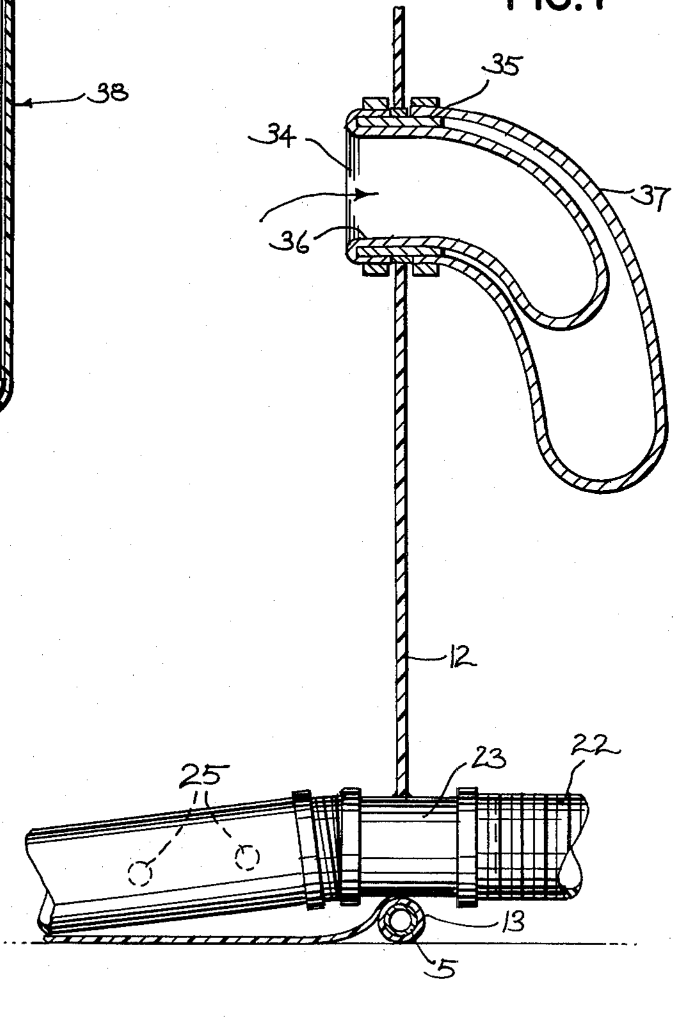

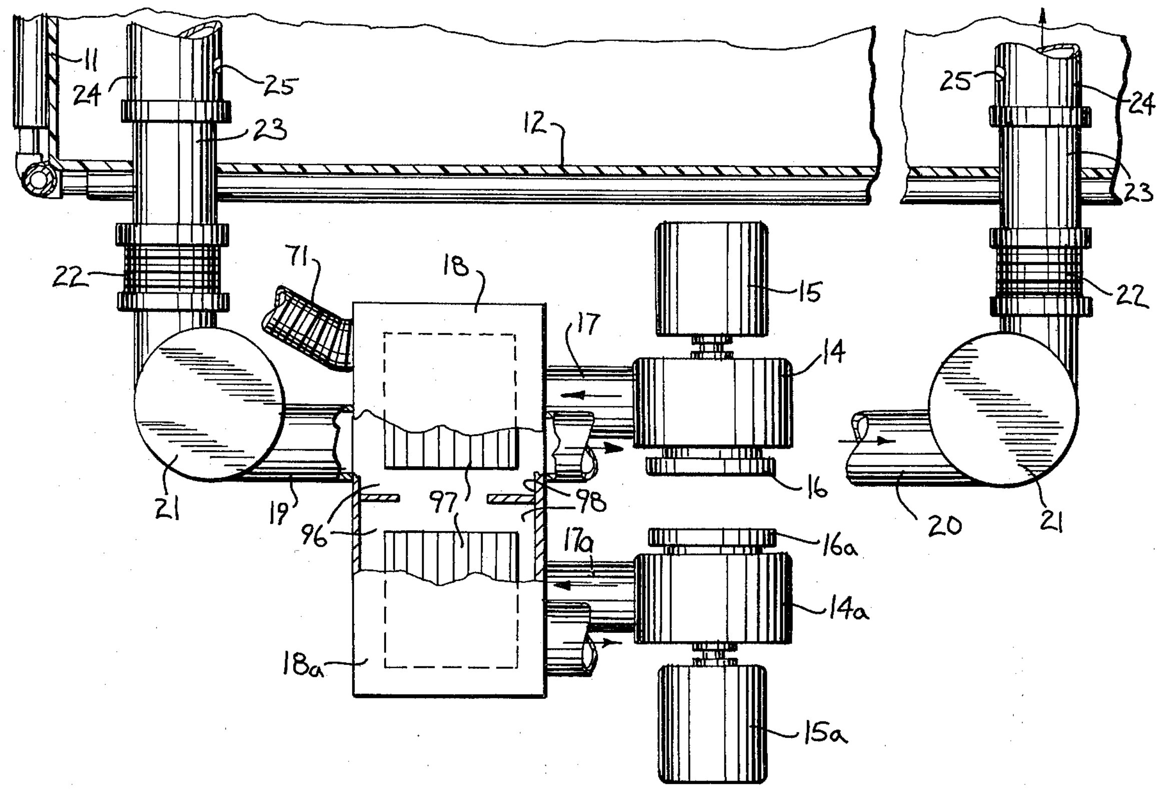
FIG.5
FIG.6
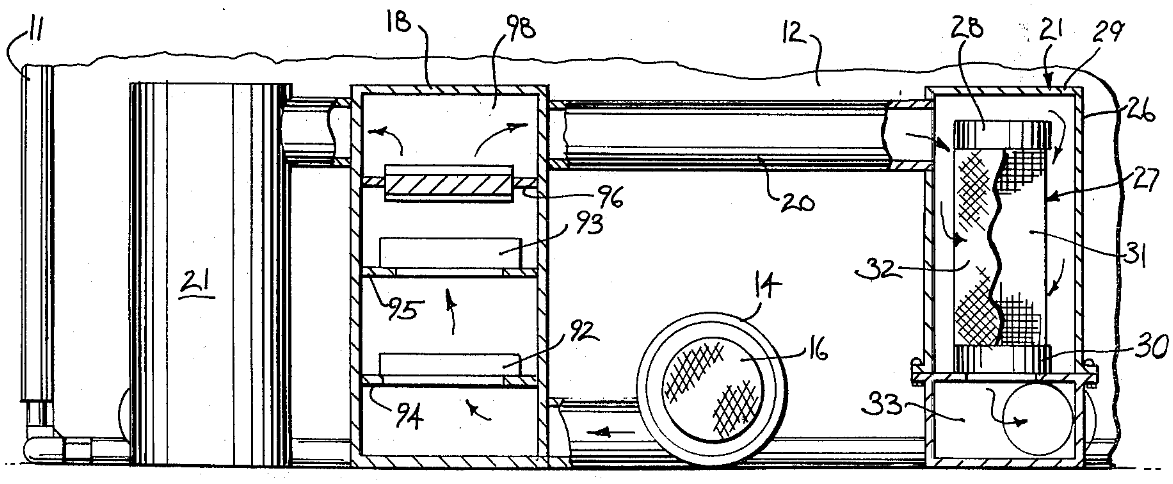

POSITIVE ENVIRONMENTAL ENCLOSURE

BACKGROUND OF THE INVENTION

Environmental enclosures are used by hospitals, animal testing facilities, chemical plants, and the like to maintain a germ-free or defined flora atmosphere. In some instances the environmental enclosure may be a small table top unit adapted to hold up to one dozen animals in a germ-free atmosphere. In other instances the enclosure may constitute a walk-in chamber or clean room of substantial size to permit the operator to walk and work within the enclosure.

One common form of clean room includes a flexible drape which extends downwardly from the ceiling and defines the clean room or chamber. In installations of this type, filtered air is introduced through the ceiling into the chamber and is discharged through the space beneath the drape for recirculation through the filter.

Another type of commonly used clean room is the fixed wall or permanent type and the clean atmosphere is achieved by circulating filtered air through the room. The permanent type clean room is extremely expensive to construct, and cannot be readily adapted for other types of usage.

In use, operators must periodically enter the clean room to inspect or tend the animals or other objects being controlled. To maintain the sterile atmosphere in the clean room, the normal procedure is for the operator to shower and put on sterile garments before entering the clean room. While this procedure is intended to maintain the sterile conditions, in practice, it is not completely effective in preventing contamination of the clean room.

As an additional problem, the clean room may contain toxic or hazardous microorganisms and in the past there has been no completely foolproof method of preventing the operator, during periods of entry into the clean room, from being contaminated with the hazardous materials, thus posing a potential health hazard to the operator and a threat of contamination to the surrounding environment.

SUMMARY OF THE INVENTION

The invention relates to a large environmental enclosure or clean room, capable of maintaining a germ-free or defined flora atmosphere and which will positively prevent contamination of the operator when working in the enclosure. In accordance with the invention, the environmental enclosure includes a structural frame which supports a flexible transparent plastic closure to provide a sealed chamber or room. Air is passed through a two-stage filter system and is introduced into the sealed enclosure through large inlet ducts which are positioned along the lower edge of the enclosure, and the air from within the enclosure is exhausted through a filter duct.

Mounted adjacent the enclosure is a small entry compartment which is also formed of transparent flexible plastic material, and the entry compartment has a sealed zippered door for access from the exterior. Similarly, a sealed zippered door provides access between the entry compartment and the main chamber.

In order to inspect animals or other material contained within the main chamber or enclosure, the operator enters the entry compartment through the zippered door and puts on a hermetically sealed suit which is normally stored within the entry compartment. The sealed suit has a provision for receiving air either from an outside compressor or from the main filtered air supply system, and for discharging air from the suit to the exterior of the entry compartment.

With the operator sealed within the suit, the entry compartment is sterilized either by use ultraviolet light or by spraying a liquid sterilant into the entry compartment. With the entry compartment sterilized, the operator then enters the main chamber through the zippered door to conduct the inspection or working operation, while retaining a completely sterile or germ-free atmosphere in the chamber.

The clean room of the invention also has a provision for operators on the outside of the enclosure to inspect animals or other materials contained within the enclosure. In this regard, the wall of the transparent plastic enclosure is provided with one or more pairs of glove ports and gloves are sealed to the ports, so that the operator may insert his hands into the gloves and inspect items contained within the enclosure. In the event the gloves may be puntured, a pouch, which is normally attached to the inner wall of the enclosure, can be sealed around the glove ports, so that the punctured glove can be removed and replaced without destroying the germ-free atmosphere in the enclosure.

The environmental enclosure of the invention is a portable unit which can be readily installed in any existing building and can be removed and stored when not needed. The enclosure is capable of maintaining a germ-free or defined flora atmosphere, as may be required for the particular clean room operation.

The operator, wearing the sealed sterilized suit, can move freely within the clean room without danger of contaminating the materials within the room and without danger of being contaminated by any microorganisms within the room. This greatly reduces the incidence of hazard to the operator.

With the structure of the invention, it is possible for a supervisory operator located on the outside of the enclosure to inspect the animals or other items within the enclosure by having the animals brought to the inspection area by a second operator who is within the enclosure. This insures that the animals, or other items, will be inspected more regularly, and eliminates the need for the supervisory operator to enter the enclosure.

Other objects and advantages will appear in the course of the following description.

DESCRIPTION OF THE DRAWINGS

The drawings illustrate the best mode presently contemplated of carrying out the invention.

In the drawings:

FIG. 2 is an enlarged fragmentary side elevation of the lower portion of the enclosure;

FIG. 3 is a section taken along line 3—3 of FIG. 2;

FIG. 4 is a fragmentary vertical section showing the inspection area;

FIG. 5 is a top plan view with parts broken away in section showing the rear portion of the enclosure and the filter system;

FIG. 6 is a rear elevation of the structure shown in FIG. 5 with parts broken away;

FIG. 7 is a vertical section taken through the rear of the enclosure;

DESCRIPTION OF THE PREFERRED EMBODIMENT

Figure 1:
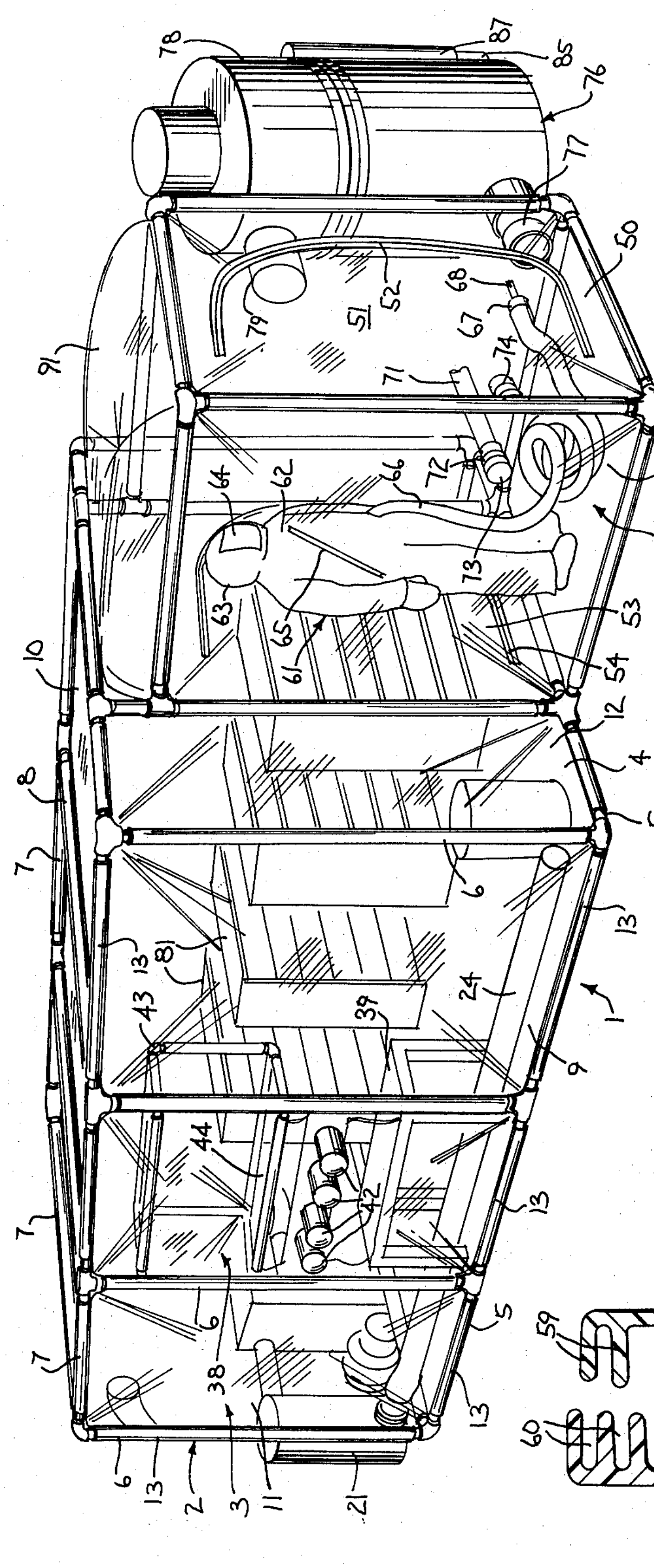
FIG. 1 is a perspective view of the environmental enclosure of the invention.

FIG. 1 is a perspective view of the environmental enclosure 1 or clean room of the invention. The enclosure 1 includes a tubular structural frame 2 which supports a transparent plastic sheet 3 that defines sealed chamber 4.

The frame 2 includes a series of base members 5 which support vertical columns or posts 6, and upper horizontal supports 7 are connected to the upper ends of the posts 6. In addition, a series of cross members 8 extend across the top of the frame between the posts 6.

The plastic sheet material 3 is preferably formed of polyurethane film and includes a bottom wall 9, a top wall 10, a pair of side walls 11 and a pair of end walls 12, which are sealed together to provide an air tight enclosure. The outer surface of the plastic enclosure is provided with elongated loops 13 which receive the respective structural support members of the frame to thereby support the plastic enclosure from the frame, as best shown in FIGS. 2 and 3.

To supply filtered air to the chamber 4, a blower or fan 14 is located along the end wall 12 of the enclosure and is driven by a motor 15. Located adjacent the inlet to the blower is a pre-filter screen 16, and air is drawn into the blower through the screen and discharged through duct 17 to the lower end of filter unit 18. The filter 18 is a conventional HEPA filter which is capable of removing up to 99.9% of particulate material having a size greater than 0.3 microns.

The air discharged from the filter 18 is conducted through ducts 19 and 20 to the second stage filters 21, and the air is discharged from the filters 21 through ducts 22, which communicate with the chamber 4. As shown in FIG. 5, the inner end of each duct 22 is connected through a rigid conduit 23 which is sealed to the plastic sheet 3, to a pipe 24 which rests on the bottom wall 9 and extends substantially the full length of the enclosure. Each pipe 24 is provided with a plurality of openings 25 which are spaced along the length of the pipe, and the filtered air is distributed through the openings into the chamber 4. With this air supply system, the air will be uniformly distributed throughout the entire length of the chamber to minimize drafts within the chamber.

The second stage filters 21 are best illustrated in FIG. 6. The air enters the upper portion of each filter 21 tangentially through the duct 20, which communicates with the annular space between the outer casing 26 and the central filter assembly 27. The filter assembly 27 includes an upper head 28, located beneath the cover 29 of the filter, and a lower head 30. A tubular support 31 having an open construction connects the heads 28 and 30, and a filter element 32, composed of a number of superimposed layers of fiber glass is wrapped around the tubular support. The interior of the tubular support 31 communicates through a passage 33 in the lower head 30 with the duct 22. With this construction, the air from filter 18 enters the filter 21 tangentially and spirals within the annular space before being discharged through the filter element 32 and passage 33 to the outlet duct 22. The air being discharged from the filters 21 through duct 22 is germ-free.

The air is discharged from chamber 4 through an outlet 34 located in the upper portion of end wall 12. Each outlet includes a rigid tube 35 sealed within an opening in the wall 12 and an inner porous filter sock 36 is clamped to the inner end of tube 35, while a second filter sock 37 is clamped to the outer end of tube 35. As shown in FIG. 7, the socks 36 and 37 provide a two-stage filter system for the discharge of air from chamber 4. The construction enables the sock 36 to be removed and replaced from the inside of the chamber, while the sock 37 can be removed from the outside. During removal of either sock, the second sock, along with the positive pressure within the chamber, will prevent the entry of foreign materials through the outlet. If toxic or hazardous materials are contained within the chamber 4, a more elaborate filter system can be associated with outlet 34 to prevent the toxic or hazardous materials from contaminating the surrounding environment.

In order to permit an operator standing on the outside of the enclosure to inspect animals or other items contained in the enclosure, an inspection area is provided in one of the side walls, as indicated by 38. A table 39 is located within the chamber 4 beneath the inspection area 38. Positioned in the side wall 11 at a level above the table 39 are a plurality of glove ports 40, and gloves 41 are connected through sleeves 42 to the glove ports, so that the operator, by standing on the outside of the enclosure, and inserting his hands within the gloves 41 can inspect animals or other objects on the table 39. Located above the glove ports 40 is a small tubular frame 43, and the side wall 11 of the sheet material 3 extends inwardly over the frame to define the viewing or inspection station 38 which is offset inwardly from the main portion of the side wall 11, as shown in FIG. 4. The horizontal portion 44 of the side wall 11 extending over the table 39 is formed of optically clear plastic film so that the operator, by inserting his head within the viewing area, can look downwardly through the section 44 of the side wall at the animals or other objects on the table 39.

The gloves 41 may accidentally be punctured either by surgical instruments or by the animals or other objects and to maintain the germ-free conditions of the chamber 4 in the event of a puncture of the gloves, a sealing pouch 45 is attached to the inner surface of the side wall 11. The lower edge of the pouch 45 is permanently sealed to the side wall 11 while the remaining edges of the pouch can be connected to the side wall by means of a detachable plastic sealing strip 46.

In normal use, the pouch 45 hangs downwardly alongside the inner surface of the side wall 11. However, in the event of a puncture of the gloves 41, an operator located within the chamber 4 can seal the pouch 45 to the side wall of the chamber, and the operator on the outside of the chamber can then remove his hands from the gloves and replace the punctured glove, without destroying the sterile atmosphere in the chamber. Before detaching the sealing strip 46 a sterilizing agent is sprayed into the space between the pouch 45 and the side wall 11 as this area has been exposed to the atmosphere when the glove was replaced.

To prevent contamination of material within the chamber 4 by operators working therein, and to protect the operator from microorganisms or other toxic materials contained within the chamber, an entry compartment 47 is associated with the enclosure 1. The entry compartment 47 includes a structural frame 48, similar to frame 2, that is enclosed by transparent flexible plastic film 49 which is sealed to the sheet material 3.

The outer wall 50 of the entry compartment 43 is provided with a door 51 or closure, that is sealed to the wall 50 by a double zipper seal assembly 52. Similarly, the end wall 12, adjacent the entry compartment 47, of the enclosure is provided with a door 53 or closure, which provides communication between the entry compartment 47 and the main chamber 4, and the door is sealed by U-shaped single zipper seal assembly 54.

Figure 8:
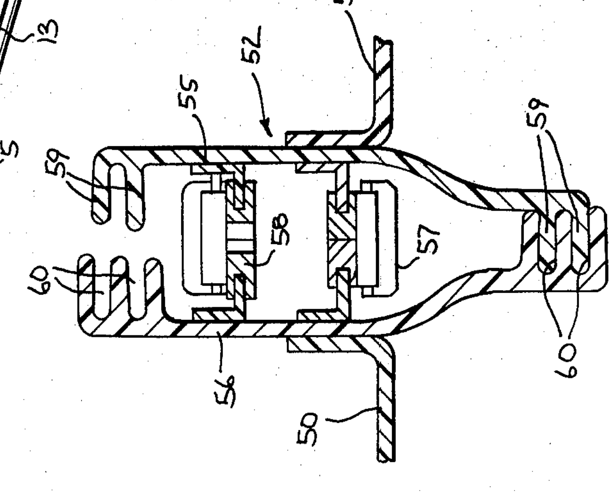
FIG. 8 is a section taken through the zippered door of the entry compartment.

The double zipper seal assembly 52 is best illustrated in FIG. 8. The side walls 55 and 56 of the zipper assembly 52 are sealed to the plastic sheet material of wall 50, and a pair of standard zippers 57 and 58 are connected between the side walls 55 and 56. Ribs 59 are formed on the ends of side member 55 which mate with a series of grooves 60 formed in the opposite side member 56. When the ribs 59 are inserted within the respective grooves 60, an air tight seal is provided along the length of the seal assembly. As shown in FIG. 8, the seal associated with the zipper 57 is in the closed position, while the seal associated with the zipper 58 is in the open position. With this double zipper construction, the door 51 can be opened from either side.

The zipper assembly 54 is similar to zipper assembly 52, except that the zipper 54 assembly includes only a single zipper and seal because it is only necessary to seal the door from the outside when the operator leaves the main chamber 4 and enters the compartment 47.

The operator who enters the entry compartment through the door 51 puts on a hermetically sealed suit 61 which is normally stored within the entry compartment 47. The suit 61 includes a body portion 62 and a helmet 63 provided with a viewing window 64. The suit can be sealed by means of a single zipper seal assembly 65, similar in construction to the seal assembly 54, which extends across the front of the body portion 62 of the suit.

Figure 10:
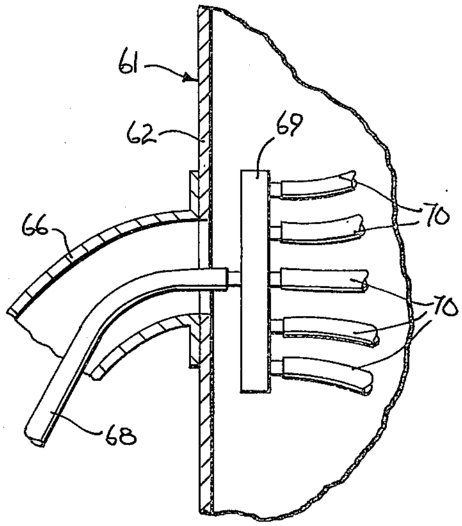
FIG. 10 is a section showing the connection of the air supply and air discharge conduits to the operator's suit.
Figure 12:
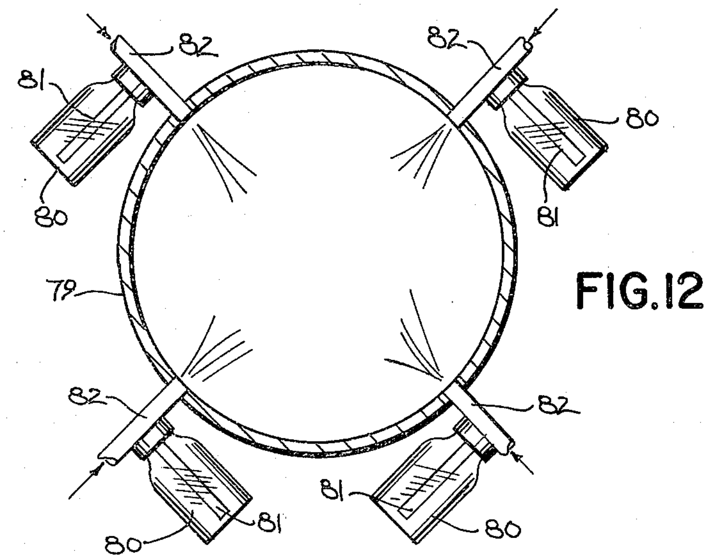
FIG. 12 is a section taken along line 12—12 of FIG. 11.

While the operator is wearing the suit 61, he is provided with a self-contained air system. In this regard, a hose 66 is sealed within an opening in the waist portion of the body portion 62 of the suit, and the hose, which has a substantial length, is connected to a rigid conduit 67 which is sealed within an opening in the transparent plastic covering 49. An air line 68, which is connected to a suitable source of air under pressure, extends through the conduit 67 and hose 66 into the suit 61 and is connected to a manifold 69. As shown in FIG. 10, five lines 70 extend from the manifold 69. A line 70 extends into each of the legs of the suit 61 to the area of the ankles, a line extends into each of the arms of the suit, to the position of the wrist, and the other line extends to the lap of the helmet 63 for breathing purposes. With this system air is supplied to the interior of the suit not only for breathing, but also for cooling. An open microphone, not shown, is also located in the helmet portion 63 of the suit to enable the operator's breathing to be monitored and to provide communication between the operator and personnel on the outside of the chamber.

The hose 66 has a substantial length and can be stored in coiled form within the entry compartment 47. When the operator enters the the chamber 4 through the door 53 the hose 66 will trail behind him. In some instances, depending on the size of the chamber 4, an overhead rail can be provided and the operator can hook the hose 66 onto the rail so that the hose will not drag along the floor as the operator moves within the chamber 4.

Figure 9:
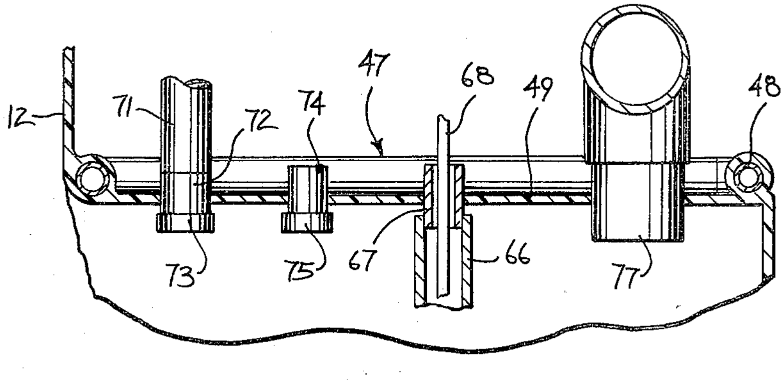
FIG. 9 is a horizontal section taken through the entry compartment and showing the air supply and discharge system.

The entry chamber also provides an alternate form of supplying and discharging air to the hermetically sealed suit 61 and in this system, filtered air from the filter 18 is utilized. An air line 71 is connected between the filter 18 and a rigid conduit 72 which is sealed within the plastic covering 49 of the entry chamber 47, and the line 71 is located outside of the enclosure 1. As shown in FIG. 9, the conduit 72 is closed off by a cap 73, but in the event the filtered air is to be employed for breathing and cooling purposes within the suit 61, the conduit 72 is conected through a hose, not shown, to a connection on the suit 61 to supply filtered air to the suit. Air from the suit is discharged through a second hose, not shown, which is connected to the rigid conduit 74, sealed within the covering 49 of the entry compartment. Again the conduit 74 is shown as closed by a cap 75. Thus, if the compressed air system shown by the air line 68 is employed, the conduits 72 and 74 are closed off. If the alternate system using filter air is employed, the conduit 66 will be closed off, and the conduits 72 and 74 will be connected through hoses to the operator suit 61.

Figure 11:
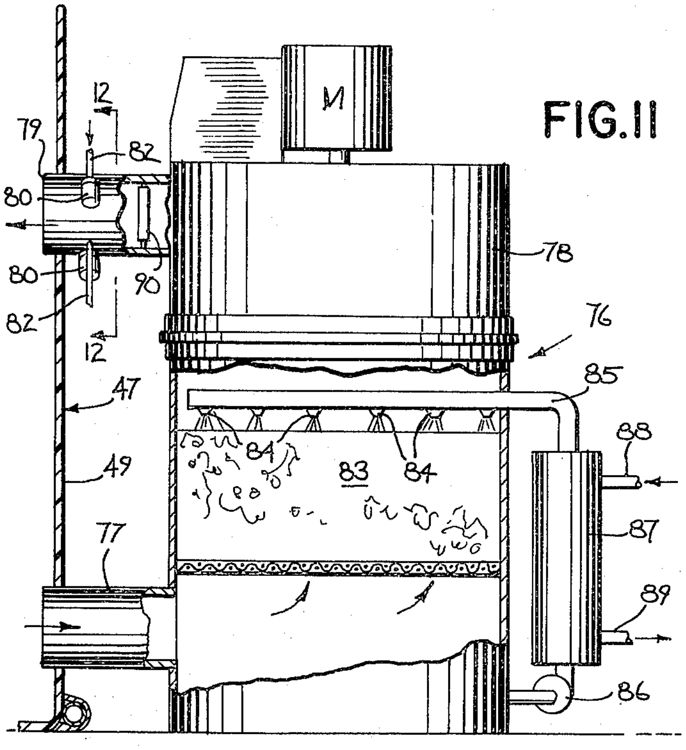
FIG. 11 is a side elevation with parts broken away showing the scrubbing unit.

After the operator is sealed within the suit 61, the suit, as well as the entire interior of the entry compartment 47, is sterilized, preferably by spraying a sterilizing agent into the entry compartment. To provide this function a combined sterilizing unit and scrubber 76 is utilized. A duct 77, as best shown in FIG. 11, is connected in sealed relation to the lower portion of the covering 49 of the entry compartment 47 and is connected to the lower end of the scrubbing unit 76. The upper end of the scrubbing unit 76 includes a fan or blower 78 and the discharge of the fan is connected through a return conduit 79 to the upper portion of the entry compartment. An aqueous solution of a liquid sterilizing agent is contained within a series of jars 80 which are mounted on the outer surface of the return duct 79, and the sterilizing liquid is drawn from each jar through a tube 81 into a high velocity air line 82 by an aspirating action. The lines 82 are connected to a suitable source of air under pressure 82a and the high velocity air streams will draw the sterilizing agent into the lines 82 for delivery into the duct 79 and then to the entry compartment 47. During the sterilizing cycle, air containing the atomized sterilant will be drawn upwardly through the unit 76 by operation of the blower 78, thereby sterilizing objects within the entry compartment 47, as well as the interior of the scrubbing unit. After the sterilizing liquid from jars 80 has been atomized and distributed into the entry compartment, the operation of the blower 78 is terminated for a period of time sufficient to provide the sterilization, generally about 5 minutes. After sterilization is complete, the blower 78 is again operated to circulate the air from the entry compartment through the scrubbing unit 76 and a scrubbing liquid is passed countercurrently to the flow of air in the scrubbing unit to remove the sterilant from the air. To provide the scrubbing action, the scrubbing unit includes a generally cylindrical housing that contains a bed 83 of an inert material, such as polypropylene rings, and a scrubbing liquid, such as water, sodium hydroxide, sodium carbonate, or sodium bicarbonate, is sprayed over the bed by spray nozzles 84 and flows countercurrently to the flow of air entering the housing through the duct 77 to dissolve the vaporized sterilizing liquid in the air stream. A line 85 connects the spray nozzles with the bottom of the housing and the scrubbing liquid is circulated through the line by a pump 86. The scrubbing liquid is cooled by passing it through a chiller or heat exchanger 87, and a coolant, such as water, is supplied to the chiller through line 88 and is withdrawn through line 89. In addition, an electrical heating element 90 is positioned in the return duct 79 between the blower 78 and the sterilizing jars 80. During the scrubbing cycle, the heating element 90 will act to heat the air being returned to the entry compartment. By heating the air entering the entry compartment, additional moisture, resulting from the spraying of the aqueous solution of the sterilizing agent into entry compartment 47, can be absorbed in the air, and the absorbed moisture will be released as the circulating air is cooled in the scrubbing unit 76.

The top wall 91 of entry compartment 47 is normally disposed in a downwardly sagging condition. A substantial volume of air is added to the entry compartment during the sterilizing cycle through the air lines 82, and to accommodate the additional volume, the wall 91 will bulge or deflect upwardly, as illustrated in FIG. 1.

The invention also includes a provision for preventing interruption of the filtered air supply to the chamber or clean room 4 during periods when the filters are being replaced, or in the event a malfunction occurs in the motor 15 or blower 14. In this regard, a second fan or blower **14*a* having a filtered air intake 16*a* is positioned alongside the blower 14, and the blower 14*a* is driven by a motor 15*a*. The outlet 17*a* of blower 14*a* is connected to the lower end of a second filter unit 18*a* which is disposed in side-by-side relation with the filter 18**.

Each filter 18 and **18*a* includes first and second stage filters 92 and 93 which are supported on walls 94 and 95 respectively. Located across the upper end portion of each of the filters 18,18*a* is a wall 96 having an opening which is enclosed by a power operated louvered air valve 97. The upper compartments 98 located above the respective air valves of the two filters 18,18*a* are joined together so that air flowing upwardly through either of the air valves 97 will be discharged through the conduits 19 and 20**.

In normal operation, one of the motors **15,15*a* is operated to supply filtered air to the chamber 4. If operation of that motor is stopped for some reason, either through a malfunction, or for the purpose of changing filters in the filter unit, a control circuit is programmed to close the air valve associated with that motor and to start the other motor and open its corresponding air valve. For example, if the motor 15 is stopped, the air valve 97 of filter 18 will close, and air valve 97 of filter 18*a* will open and the motor 15*a* will start so that the supply of air through ducts 19 and 20 will not be interrupted. It is also contemplated that indicator lights on a control panel will be lighted when the operation of motor 15** is discontinued, as a signal to the operator.

While the above description has shown the enclosure 1 and the entry compartment to be generally rectangular in shape, it is contemplated that the enclosure and entry compartment can have any desired shape or size.

To enter the chamber 4 to inspect the animals or other objects which may be contained within racks 81 in the chamber, the operator unseals the zippered seal assembly 52 and enters the entry compartment 47. After resealing the door 51, the operator puts on the suit 61 which is normally stored in the entry compartment. With the operator sealed within the suit 61, the entry compartment is sterilized by introducing the sterilizing agent through the spray nozzles 84, or alternately ultraviolet light can be used for the sterilization. After a sufficient period of time to insure complete sterilization of all items within the entry compartment, the scrubbing unit 78 can be operated to remove the sterilant from the atmosphere of the entry compartment and the operator can enter the chamber 4 by unsealing the zipper seal assembly 54.

The operator can move freely within the chamber 4 with the air supply hose 68 and air discharge hose dragging behind him on the floor. As previously noted, if a supervisory operator on the outside of the enclosure wishes to inspect any of the animals or objects within the enclosure, the operator within the enclosure can place the animal on the table 39 where it may be inspected by the supervisory operator using the gloves 41 in the glove ports 40.

After inspection and tending of the animals has been completed, the operator returns to the entry compartment 47 and seals the seal assembly 54. With the chamber 4 sealed off, the operator can then remove the suit 61 and leave the entry compartment through the door 51.

The environmental enclosure of the invention is a portable unit which can be installed in existing buildings, and if not being used, can be readily dismantled and stored.

Due to the use of the sterilized entry compartment and the hermetically sealed suit which has its own air supply, there is no danger of contamination of the atmosphere within the chamber 4 by the operator will not be contaminated by any microorganisms, carcinogens, or other chemicals contained within the chamber 4.

While the above description has shown a positive super-atmospheric pressure being utilized in the chamber 4, it is contemplated that in certain situations a negative pressure can be used in the chamber.

Various modes of carrying out the invention are contemplated as being within the scope of the following claims particularly pointing out and distinctly claiming the subject matter which is regarded as the invention.

I claim:

1. An environmental enclosure, comprising closure means for defining a hermetically sealed chamber, filter means for supplying filtered air to the chamber, a hermetically sealed suit disposed within the chamber and worn by an operator, an air discharge hose having one end sealed to the suit and the opposite end of the hose being sealed to the wall of said closure means whereby air from within the suit is discharged through the hose to the exterior of the closure means, and an air supply conduit disposed within the hose, one end of the air supply conduit being in communication with the interior of the suit and the other end of the air supply conduit communicating with the exterior of the chamber, whereby air is supplied through said conduit to the interior of the suit.

2. The enclosure of claim 1, wherein said suit includes a body portion, a pair of arms a pair of legs, and a head portion, a manifold connected to the air supply conduit and located within the suit, and a plurality of air lines connected to the manifold for supplying air to said arms, said legs and the head portion of the suit.

3. The enclosure of claim 1, wherein said opposite end of the air supply conduit is connected to said filter means, whereby filtered air is supplied to said suit.

4. In an environmental enclosure, a structural frame, a closed flexible transparent covering supported by the frame and defining a sealed chamber, said covering having a side wall, and said side wall having an opening enclosed by a flap integrally connected to said wall, a zipper interconnecting the flap and said wall, and sealing means disposed on at least one side of the wall and extending the complete length of said zipper for sealing said zipper against the passage of air, said sealing means comprising a first sealing element connected to the flap and a second sealing element connected to the wall and releasably connected to said first element to provide the seal.

5. The enclosure of claim 4, wherein one of said sealing elements is provided with a groove extending the length of the zipper and the other of said sealing elements is provided with an elongated projection to be received within the groove to provide the seal.

6. In an environmental enclosure, a structural frame, a closed flexible transparent covering supported by the frame and defining a sealed chamber, said covering having a side wall, a plurality of glove ports located in said side wall, a glove sealed to each glove port whereby an operator by inserting his hands within the gloves can inspect objects located within the chamber, a pouch disposed within the chamber, means for securing a portion of the periphery of the pouch to the inner-surface of said side wall, and sealing means for removably sealing the remaining portion of the periphery of the pouch to the inner surface of the side wall around said glove ports to thereby seal off said glove ports and said gloves from said chamber.

7. The enclosure of claim 6, wherein said pouch has a first edge permanently secured to the inner surface of said side wall, and said sealing means including a first sealing element extending around the remaining edge of said pouch and a second sealing element attached to said side wall and disposed to be engaged by said first sealing element.

8. An environmental enclosure, comprising closure means defining a sealed chamber, said closure means including a structural frame and a flexible covering supported by the frame, means for supplying filtered air to the chamber, means for exhausting air from the chamber, an entry compartment disposed adjacent said chamber, a first sealed access door connecting the entry compartment with said chamber, a second sealed access door providing communication between the entry compartment and the exterior, a hermetically sealed suit disposed in the entry compartment and worn by an operator, means for supplying air to the interior of said suit, means for exhausting air from the interior of the suit to the atmosphere, sterilizing means for spraying a sterilant in the entry compartment to sterilize objects therein, a scrubbing unit, first conduit means for conducting air from the entry compartment to said scrubbing unit, and second conduit means for returning the air from the scrubbing unit to the entry compartment, said scrubbing unit acting to remove the sterilant from the air, said scrubbing unit including a bed of generally inert material, means for flowing the air through the bed, means for flowing a scrubbing liquid through the bed in countercurrent flow to the flow of air through the bed, cooling means for cooling the scrubbing liquid prior to flowing the scrubbing liquid through the bed to thereby cool the air, and heating means disposed in said second conduit means for heating the air prior to its return to the entry compartment.

9. An environmental enclosure, comprising closure means defining a sealed chamber, said closure means including a structural frame and a flexible covering supported by the frame, means for supplying filtered air to the chamber, means for exhausting air from the chamber, an entry compartment disposed adjacent said chamber, a first sealed access door connecting the entry compartment with said chamber, a second sealed access door providing communication between the entry compartment and the exterior, a hermetically sealed suit disposed in the entry compartment and worn by an operator, means for supplying air to the interior of said suit, means for exhausting air from the interior of the suit to the atmosphere, sterilizing means for spraying a sterilant in the entry compartment to sterilize objects therein, a scrubbing unit, first conduit means for conducting air from the entry compartment to said scrubbing unit, and second conduit means for returning the air from the scrubbing unit to the entry compartment, said scrubbing unit acting to remove the sterilant from the air, said sterilizing means comprising a container of said sterilant mounted adjacent said second conduit means, and aspirating means for drawing the sterilant from the container into said second conduit means.

10. The enclosure of claim 9, wherein said aspirating means includes a high velocity air line connected between a source of air under pressure and the second conduit means, whereby flow of air through said air line will draw the sterilizing agent from the container and entrain the sterilizing agent in the high velocity air stream.

11. The environmental enclosure of claim 10, wherein said entry compartment includes an expandable section capable of expanding outwardly to accommodate an increase in air volume in the entry compartment due to entry of the air through said high velocity air line.

12. The environmental enclosure of claim 11, wherein said section comprises a top wall of the entry compartment, said top wall normally disposed in a downwardly sagging condition and said increased volume causing said top wall to expand upwardly.

* * * * *